United States Patent
Smith et al.

(10) Patent No.: US 9,079,176 B1
(45) Date of Patent: Jul. 14, 2015

(54) REGENERATION OF AN ACIDIC IONIC LIQUID CATALYST BY ADDITION OF BRøNSTED ACIDS

(71) Applicant: UOP LLC, Des Plaines, IL (US)

(72) Inventors: Stuart Smith, Lake Zurich, IL (US); Alakananda Bhattacharyya, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/229,329

(22) Filed: Mar. 28, 2014

(51) Int. Cl.
*B01J 38/60* (2006.01)
*B01J 31/40* (2006.01)

(52) U.S. Cl.
CPC .................................. *B01J 31/4053* (2013.01)

(58) Field of Classification Search
CPC ............. B01J 38/60; B01J 38/48; B01J 37/30
USPC ........................ 502/27, 22, 12, 514, 515, 518
See application file for complete search history.

(56) References Cited

U.S. PATENT DOCUMENTS

| | | | |
|---|---|---|---|
| 7,651,970 B2 | 1/2010 | Elomari et al. | |
| 7,666,811 B2 | 2/2010 | Elomari et al. | |
| 7,674,739 B2 | 3/2010 | Elomari et al. | |
| 7,674,740 B2 | 3/2010 | Harris et al. | |
| 7,678,727 B2 | 3/2010 | Harris et al. | |
| 7,691,771 B2 | 4/2010 | Harris et al. | |
| 7,727,925 B2 | 6/2010 | Elomari et al. | |
| 7,732,363 B2 | 6/2010 | Elomari et al. | |
| 7,737,067 B2 | 6/2010 | Elomari et al. | |
| 7,737,363 B2 | 6/2010 | Kambe | |
| 7,754,636 B2 | 7/2010 | Elomari et al. | |
| 7,825,055 B2 | 11/2010 | Elomari et al. | |
| 7,956,002 B2 | 6/2011 | Elomari et al. | |
| 7,956,230 B2 | 6/2011 | Timken et al. | |
| 7,995,495 B2 | 8/2011 | Lin | |
| 8,524,623 B2 | 9/2013 | Timken et al. | |
| 2010/0331599 A1 | 12/2010 | Subramaniam et al. | |
| 2013/0303358 A1 | 11/2013 | Elomari et al. | |

*Primary Examiner* — Edward Johnson

(57) ABSTRACT

A method for regenerating deactivated acidic ionic liquid catalyst containing conjunct polymer is described. The method includes contacting the deactivated acidic ionic liquid catalyst containing the conjunct polymer with at least one Brønsted acid in a regeneration zone under regeneration conditions, resulting in a mixture comprising regenerated acidic ionic liquid catalyst, the Brønsted acid, the released conjunct polymer. The Brønsted acid is derived from a mineral acid and contains at least one organic group. The released conjunct polymer can be separated from the regenerated acidic ionic liquid catalyst and the at least one Brønsted acid.

20 Claims, 1 Drawing Sheet

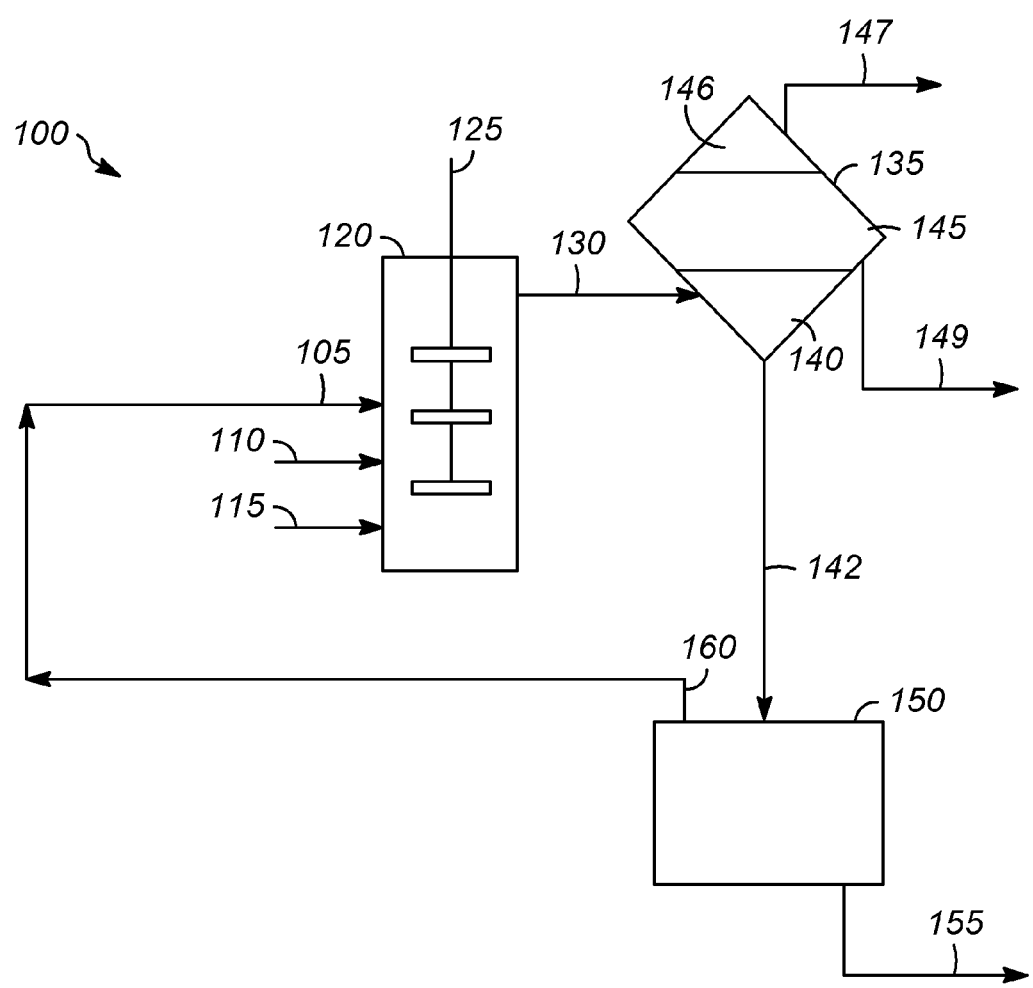

REGENERATION OF AN ACIDIC IONIC LIQUID CATALYST BY ADDITION OF BRøNSTED ACIDS

BACKGROUND OF THE INVENTION

Commercially, the alkylation of isoparaffins is catalyzed by acids such as sulfuric acid and hydrofluoric acid. Conjunct polymer (acid soluble oils (ASO), also known as red oil) forms as a byproduct of the alkylation reaction, as well as other hydrocarbon reactions. When too much conjunct polymer is present, the acid catalyst loses its effectiveness. The acid must be replaced with stronger acid, or the conjunct polymer must be removed in order to reactivate the catalyst. With sulfuric acid as the catalyst, the ASO is burned, and with hydrofluoric acid, the hydrofluoric acid is distilled away from the ASO. Sulfuric acid and hydrofluoric acid are hazardous and corrosive, and their use in industrial processes requires a variety of environmental controls.

There has been a move to replace the use of sulfuric acid and hydrofluoric acid with more environmentally friendly materials.

One such process utilizes acidic ionic liquids as catalysts in hydrocarbon conversion processes, such as alkylation, isomerization, disproportionation, and oligomerization. Conjunct polymers are byproducts of the hydrocarbon reaction using ionic liquids, and they form a complex with the ionic liquid catalyst. The ionic liquid catalyst loses its effectiveness over time as the amount of conjunct polymer increases. It must then either be replaced or regenerated. Because ionic liquids are typically fairly expensive, processes for regenerating the ionic liquid catalysts are needed.

A variety of methods for regenerating ionic liquids have been developed. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. No. 7,651,970; U.S. Pat. No. 7,825,055; U.S. Pat. No. 7,956,002; and U.S. Pat. No. 7,732,363.

Another method involves contacting the ionic liquid containing the conjunct polymer with a reducing metal (e.g., Al) in the presence of an inert hydrocarbon (e.g. hexane), but in the absence of added hydrogen, and heating to about 100° C. The conjunct polymer will be transferred to the hydrocarbon phase, allowing for the conjunct polymer to be removed from the ionic liquid phase. See e.g., U.S. Pat. No. 7,674,739.

Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the CP to be removed from the IL phase. See e.g., U.S. Pat. No. 7,727,925.

The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727.

Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. This reaction increases the carbon count of the conjunct polymer. See e.g., U.S. Pat. No. 7,674,740.

The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771.

Still another method involves adding a basic reagent that displaces the conjunct polymer and is a part of the regeneration of the catalyst. The basic reagents are described as nitrogen-containing compounds such as amines, pyridinium compounds, or pyrrolidinium compounds. For example, a suitable substrate (e.g. pyridine) is added to the ionic liquid containing the conjunct polymer. After a period of time, an inert hydrocarbon would be added to wash away the liberated conjunct polymer. The ionic liquid precursor [1-butylpyridinium][Cl] would be added to the ionic liquid (e.g. [1-butyl-pyridinium][$Al_2Cl_7$]) containing the conjunct polymer followed by an inert hydrocarbon. After a given time of mixing, the hydrocarbon layer would be separated, resulting in a regenerated ionic liquid. The solid residue would be converted to ionic liquid by adding $AlCl_3$. The conjunct polymer is said to be a neutral species coordinated to free $AlCl_3$. The conjunct polymer is liberated when the chloride from the added ionic liquid precursor coordinates to the $AlCl_3$ to form $AlCl_4^-$. See e.g., U.S. Pat. No. 7,737,363 and U.S. Pat. No. 7,737,067.

Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623.

All of these regeneration approaches have drawbacks. Many of them cannot achieve above 90% conversion of the conjunct polymer, which then builds up in the process. Of those that can provide high levels of conversion, hydrogenation of the spent ionic liquid with supported (e.g., U.S. Pat. No. 7,691,771) and unsupported (e.g., U.S. Pat. No. 7,678,727) hydroprocessing catalysts may result in the active catalytic metals being extracted into the ionic liquid phase. Many catalyst supports also react irreversibly with the chloroaluminate anion of the ionic liquid. Although the use of metallic aluminum for regeneration (e.g., U.S. Pat. No. 7,995,495) is effective, it introduces undesirable solids handling issues into the refinery. Finely divided aluminum is pyrophoric and presents safety issues in a refining environment. This approach also results in the creation of additional $AlCl_3$, which has to be removed from the ionic liquid phase (e.g., U.S. Pat. No. 7,754,636) to avoid building up to a molar ratio relative to the ionic liquid cation at which solids will start coming out of solution and cause plugging issues.

Therefore, there remains a need for additional methods of regenerating ionic liquids used as catalysts in reactions.

SUMMARY OF THE INVENTION

One aspect of the invention involves a method for regenerating deactivated acidic ionic liquid catalyst containing conjunct polymer. In one embodiment, the method includes contacting the deactivated acidic ionic liquid catalyst containing the conjunct polymer with at least one Brønsted acid in a regeneration zone under regeneration conditions, the at least one Brønsted acid being derived from a mineral acid and containing at least one organic group resulting in a mixture comprising regenerated acidic ionic liquid catalyst, the at least one Brønsted acid, and the released conjunct polymer; and separating the released conjunct polymer from the regenerated acidic ionic liquid catalyst and the at least one Brønsted acid.

BRIEF DESCRIPTION OF THE DRAWING

The FIGURE illustrates one embodiment of a method for regenerating deactivated acidic ionic liquid catalyst containing conjunct polymer according to the present invention.

DETAILED DESCRIPTION OF THE INVENTION

It has been discovered that deactivated acidic ionic liquid catalysts containing conjunct polymer can be regenerated using a reagent that contains no added metals and that reacts at mild conditions. The reagent is a Brønsted acid derived from a mineral acid, such as HCl or a similar acid. Contacting the deactivated acidic ionic liquid catalyst with the regenerating reagent permits the extraction of the conjunct polymer with a suitable solvent, such as hexane. After the conjunct polymer is removed, the added Brønsted acid can be removed by thermolysis and recovered, if desired.

In addition, in some cases, the Brønsted acid is more soluble with the ionic liquid than HCl is because of the presence of organic groups on the Brønsted acid.

In addition, the mild conditions under which the process can be performed may result in lower operating costs than processes requiring harsher conditions. The mild operating conditions may also result in lower capital costs due to the ability to use less expensive materials of construction.

By deactivated acidic ionic liquid catalysts containing conjunct polymer, we mean acidic ionic liquid catalysts that have been used in hydrocarbon conversion processes, and in which conjunct polymers have formed. The conjunct polymer is bound to the ionic liquid, and it cannot be separated from the ionic liquid without some type of reaction. Washing with a solvent will not remove the conjunct polymer from the ionic liquid. By conjunct polymer, we mean the olefinic, conjugated cyclic hydrocarbons that form as a byproduct of various hydrocarbon conversion processes, including but not limited to alkylation, oligomerization, isomerization, and disproportionation.

By acidic ionic liquid, we mean an ionic liquid capable of catalyzing reactions typically carried out with an acid. As known in the art, acids such as sulfuric acid and hydrofluoric acid are often used to catalyze these reactions. These reactions include, e.g. alkylation, oligomerization, isomerization, and disproportionation. Oftentimes the acids employed in these reactions have Hammett acidity functions ($H_0$) less than 7, or less than 5, or less than 3, or less than 0, or less than –3, or less than –5, or less than –7, or less than –9. If the ionic liquid does not possess an acidic proton in its structure (e.g. 1-butyl-3-methylimidazolium heptachloroaluminate), addition of an exogenous acid is acceptable, provided the Hammett acidity function ($H_0$) of the added acid is less than 7 within the ionic liquid, or less than 5, or less than 3, or less than 0, or less than –3, or less than –5, or less than –7, or less than –9.

By the Brønsted acid being derived from a mineral acid, we mean that the Brønsted acid was formed from the reaction of a mineral acid with a base to generate the protonated complex, which has become a Brønsted acid.

The contact of a Brønsted acid with an acidic ionic liquid catalyst that contains conjunct polymer releases the conjunct polymer from the acidic ionic liquid catalyst. The conjunct polymer can be separated from the Brønsted acid and the acidic ionic liquid catalyst. The Brønsted acid can then be removed from the acidic ionic liquid catalyst, if desired. In other embodiments, the Brønsted acid can remain in the catalyst phase with the ionic liquid. The ionic liquid which has been separated from the conjunct polymer can then be sent to a hydrocarbon conversion process. Depending on the reaction conditions of the hydrocarbon conversion process, the activity of the regenerated ionic liquid can be further enhanced by the addition of an acid additive. If the Brønsted acid is removed from the acidic ionic liquid catalyst, it can be recycled to the regeneration zone. The acidic ionic liquid catalyst can be recycled to a hydrocarbon conversion process.

In some embodiments, the deactivated acidic ionic liquid catalyst containing the conjunct polymer is contacted with the Brønsted acid in the presence of a solvent which is immiscible with the ionic liquid. In this situation, two phases will result: one containing the regenerated ionic liquid and the Brønsted acid, and the other containing the released conjunct polymer. The conjunct polymer can then be removed from the solvent, and the solvent can be recycled.

In other embodiments, the solvent immiscible with the ionic liquid is added after the contacting step in order to separate the conjunct polymer from the regenerated ionic liquid.

In some embodiments, no solvent is required to separate the conjunct polymer from the regenerated ionic liquid. Although solvent is not always necessary, it will maximize recovery, removal, and separation of the conjunct polymer.

In some embodiments, the deactivated acidic ionic liquid catalyst containing the conjunct polymer is diluted with a solvent which is miscible with the ionic liquid forming a homogeneous solution. This homogeneous solution of the deactivated acidic ionic liquid catalyst containing the conjunct polymer and the miscible solvent is contacted with the Brønsted acid.

The contacting step can be done in the presence of the immiscible solvent, or the immiscible solvent can be added afterward to separate the conjunct polymer, as discussed above.

The deactivated acidic ionic liquid catalyst and the Brønsted acid are contacted for a period of time sufficient to allow the Brønsted acid to react with the conjunct polymer and/or the ionic liquid. This will typically take in the range of about 5 sec to about 24 hr, or about 1 min to about 24 hr, or about 10 min to about 24 hr, or about 10 min to about 15 hr, or about 10 min to about 10 hr, or about 10 min to about 5 hr, or about 30 min to about 5 hr, or about 1 hr to about 3 hr.

The contacting typically takes place at a temperature in the range of from about –20° C. to the decomposition temperature of the acidic ionic liquid catalyst. A typical temperature range is about –20° C. to about 200° C., or about 20° C. to about 150° C., or about 20° C. to about 125° C., or about 20° C. to about 100° C., or about 20° C. to about 75° C., or about 20° C. to about 50° C. In some embodiments, the contacting takes place at room temperature.

The pressure is typically ambient pressure, although higher or lower pressures could be used if desired. The pressure is typically determined by the vapor pressure of the solvent used. In some embodiments, the reaction can be run in the presence of hydrochloric acid, which may assist in the removal of the conjunct polymer from the ionic liquid. The partial pressure of hydrochloric acid can be in the range of about 0 to about 13790 kPa, or about 0 to about 6900 kPa, or about 0 to about 3447 kPa, or about 0 to about 2758 kPa, or about 0 to about 2068 kPa, or about 0 to about 1379 kPa, or about 0 to about 689 kPa, or about 0 to about 345 kPa, or about 0 to about 172 kPa, or about 0 to about 103 kPa.

The molar ratio of the Brønsted acid to the ionic liquid is typically greater than about 1:1 for a heptachloroaluminate anion.

If the reaction rate of the Brønsted acid with the conjunct polymer is too slow, a catalyst can be added to increase the rate. Suitable catalysts include, but are not limited to, metals or compounds of Au, Ru, Rh, Cu, Pd, and Pt.

In some embodiments, the contacting can take place in the presence of an acid. This will typically be the mineral acid from which the Brønsted acid is derived.

The contacting can take place in any suitable process, such as solvent extraction, or contacting in one or more mixer/settlers.

The reaction will proceed simply by contacting the Brønsted acid with the acidic ionic liquid catalyst. However, the contact between the Brønsted acid and the acidic ionic liquid catalyst can be increased by increasing the mixing intensity.

The contacting step may be practiced in laboratory scale experiments through full scale commercial operations. The process may be operated in batch, continuous, or semi-continuous mode. The contacting step can take place in various ways, with both concurrent and co-current flow processes being suitable. After contacting the acidic ionic liquid catalyst and the Brønsted acid and the immiscible solvent, two phases result, a catalyst phase containing the acidic ionic liquid catalyst and an organic phase containing the conjunct polymer and the immiscible solvent, if present. In some embodiments, the phases will separate due to the density difference between the two phases. In other embodiments, other separation processes may be needed. In some embodiments, the conjunct polymer can be decanted away. Decanting can be suitable if there is enough conjunct polymer present and it separates from the acidic ionic liquid catalyst.

If the immiscible solvent is not included in the contacting step, it can be added to separate the regenerated ionic liquid from the conjunct polymer.

In other embodiments, separation can take place in the absence of an immiscible solvent. In this case, the conjunct polymer would form a separate layer which could be removed.

After separation of the conjunct polymer from the ionic liquid, the ionic liquid can be recycled to a hydrocarbon conversion process. Depending on the conditions required for the hydrocarbon conversion process, an acid additive may be added to the ionic liquid system.

If desired, the Brønsted acid can be removed from the acidic ionic liquid catalyst. Suitable processes for removing the Brønsted acid include thermolysis. The Brønsted acid and the acidic ionic liquid catalyst can then be recycled.

In one embodiment, the regeneration process is a solvent extraction process. In the solvent extraction method, an immiscible solvent and the Brønsted acid are added to the deactivated acidic ionic liquid catalyst containing the conjunct polymer. The immiscible solvent and the Brønsted acid can be pre-mixed and added together, or they can be added separately, either at the same time or sequentially.

In a system without stirring or after stirring is ended, the components can separate into two phases based on the density difference between the ionic liquid phase and the organic phase which contains the conjunct polymer. The ionic liquid and the remaining Brønsted acid will settle to the bottom, and the conjunct polymer will be on top of the ionic liquid layer. Increasing the top layer with additional solvent will increase the conjunct polymer recovery.

The deactivated ionic liquid catalyst, the solvent, and the Brønsted acid are contacted long enough for the conjunct polymer to be removed from the ionic liquid, typically about 10 min to about 24 hr. The deactivated ionic liquid catalyst, the solvent, and the Brønsted acid are typically mixed while being contacted.

The deactivated ionic liquid, the solvent, and the Brønsted acid are typically contacted at a temperature in the range of from about −20° C. to less than the decomposition temperature of the ionic liquid, or about −20° C. to about 200° C. In some embodiments, the contacting takes place at room temperature.

The mixture is then allowed to separate into two phases: an ionic liquid phase and a hydrocarbon phase. In some embodiments, separation occurs due to the density difference between the ionic liquid phase and the hydrocarbon phase. Separation typically takes on the order of a few minutes to hours; it is generally less than about 1 hr.

The hydrocarbon layer is separated from the ionic liquid. The ionic liquid can be further washed with solvent (either the same solvent used in the extraction or a different one), if desired. The conjunct polymer is extracted into the solvent layer.

In some embodiments, after separation of the conjunct polymer from the ionic liquid, the ionic liquid can be sent to a hydrocarbon conversion process. Depending on the conditions required for the hydrocarbon conversion process, an acid additive may be added to the ionic liquid system. Suitable acids and acid precursors include, but are not limited to, HCl, tert-butyl chloride, or 2-chlorobutane. The acid precursor can be any molecule that will break down to form the acid.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

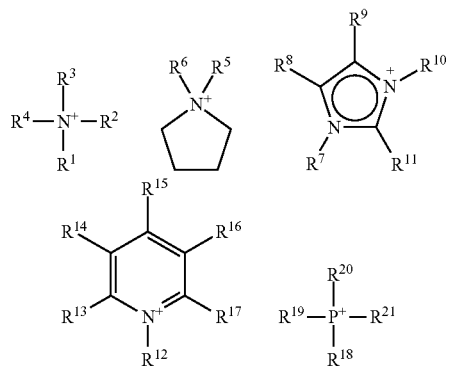

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

The Brønsted acid is derived from a mineral acid and contains at least one organic group. The acid strength of the Brønsted acid is less than the acid strength of the mineral acid from which it is derived. Suitable mineral acids include, but are not limited to, HCl, HF, HBr, HI, $H_2SO_4$, $HNO_3$, $H_3PO_4$, fluorosulfonic acids or combinations thereof. The conjugate base from which the Brønsted acid is derived is selected from the group consisting of amines, phosphines, nitrogen containing heterocycles, phosphorous containing heterocycles, pyrrolidines, imidazoles, or combinations thereof. One or more Brønsted acids can be used.

The immiscible solvent will depend on the acidic ionic liquid catalyst being regenerated. The solvent can be any solvent which is capable of forming a separate phase from the catalyst phase. There can be one or more solvents. Suitable solvents for halometallate ionic liquids (and other acidic catalysts) include, but are not limited to, paraffins, such as $C_4$ to $C_{10}$ paraffins, including n-paraffins, isoparaffins, and cyclic paraffins, and aromatic solvents. If the ionic liquid is soluble in hydrocarbons, more polar solvents which are not miscible in the ionic liquid would be used. Some polar solvents will react with the ionic liquid and so are less desirable.

The miscible solvent can be any solvent in which the ionic liquid is miscible. Suitable miscible solvents include, but are not limited to, dichloromethane.

FIG. 1 illustrates one embodiment of the process 100. The process will be described using a chloroaluminate ionic liquid, hexane ($C_6$) solvent, and trimethylammonium chloride ([$Me_3N$—H][Cl]) as the Brønsted acid.

The [$Me_3N$—H][Cl] Brønsted acid 105, the $C_6$ solvent 110, and the chloroaluminate ionic liquid containing the conjunct polymer 115 are introduced into regeneration zone 120 where they are contacted. The mixture can be stirred using a mixer 125, if desired.

The mixture 130 is sent to a settler 135, where phase separation occurs. The heavier catalyst phase 140 containing the chloroaluminate ionic liquid and the [$Me_3N$—H][Cl] Brønsted acid settles to the bottom below the lighter organic phase 145 containing the conjunct polymer and $C_6$ solvent. There may be a gas and/or vapor phase 146 which can be removed in stream 147 and further processed, if desired. The gas and/or vapor phase 146 can contain one or more of solvent, nitrogen, and HCl if a source of HCl was used (or other acids if a source of the other acid was used).

A stream 149 of the organic phase 145 containing the conjunct polymer and $C_6$ solvent is removed.

In some embodiments, a stream 142 of the catalyst phase 140 can be sent to a thermolysis zone 150 where the [$Me_3N$—H][Cl] Brønsted acid is thermally decomposed. The decomposition products, [$Me_3N$] and [HCl], 160 can be removed, leaving the regenerated chloroaluminate ionic liquid 155. In other embodiments, the Brønsted acid remains in the catalyst phase.

The regenerated chloroaluminate ionic liquid 155 can then be recycled to a hydrocarbon conversion process. The decomposition products [$Me_3N$] and [HCl] 160 of the [$Me_3N$—H][Cl] Brønsted acid can be recycled to the regeneration zone 120. In some embodiments, an acid additive is added to the regenerated chloroaluminate ionic liquid 155 (not shown) for the hydrocarbon conversion process.

EXAMPLES

Example 1

Synthesis of [("Bu)$_3$P(Hex)][$Al_2Cl_7$]

Tributylhexyl phosphonium chloroaluminate ([("Bu)$_3$P(Hex)][$Al_2Cl_7$]) is a room temperature ionic liquid prepared by mixing anhydrous tributylhexyl phosphonium chloride with slow addition of 2 moles of anhydrous aluminum chloride in an inert atmosphere. After several hours of mixing, a pale yellow liquid is obtained. The resulting acidic IL was used as the catalyst for the alkylation of isobutane with 2-butenes.

Example 2

Generation of Spent [("Bu)$_3$P(Hex)][$Al_2Cl_7$]

The spent ionic liquid samples were generated in a continuous alkylation process in which 2-butenes were contacted with tributylhexylphosphonium heptachloroaluminate ionic liquid in the presence of isobutane and 2-chlorobutane. Contacting took place in a 300 mL autoclave stirred at 1900 rpm at ambient temperature. The mixture was continuously transferred to a gravity separator, and the ionic liquid was recycled to the alkylation reactor. Flow rates and feed ratios varied over the course of the reaction which took place over several days to weeks for the various samples. At the end of each run, the heavy fraction containing ionic liquid was collected and stored under nitrogen.

Example 3

Characterization of Recovered Conjunct Polymer

The amount of conjunct polymer in the deactivated ionic liquid generated in Example 2 was determined by massing 10.13 g of the material into a vial and washing the ionic liquid with about 3×5 mL n-pentane (pre-dried using activated 3A molecular sieves) in the nitrogen glovebag. The ionic liquid was then dried under vacuum using a rotary evaporator, yielding 10.01 g of the ionic liquid. This washed and dried ionic liquid was then hydrolyzed by slowly adding the ionic liquid to crushed ice contained in a jar and extracting the aqueous layer with 35 mL of n-pentane. The n-pentane was separated from the aqueous layer, and the aqueous layer was washed two more times with n-pentane. The total volume of water/ice and n-pentane used was 75 mL and 80 mL, respectively. The combined n-pentane layers were then washed twice with 15 mL of 0.1% $Na_2CO_3$ solution and once with 20 mL of 0.1% $H_2SO_4$ solution. The separated n-pentane layer was then dried over anhydrous $MgSO_4$, filtered through fiberglass, and concentrated under vacuum to yield 0.324 g of yellow conjunct polymer, indicating that the concentration of conjunct polymer within the ionic liquid was 3.2 wt. %. The chlorine concentration within the conjunct polymer was 792 ppm as determined using the ion combustion method UOP991-12. The conjunct polymer was analyzed by simulated distillation (ASTM D2887) and is shown in Table 1 below.

Example 4

Removal of Conjunct Polymer by Reaction with Triethylammonium Chloride

The deactivated ionic liquid (6.04 g) generated in Example 2 was added to an oven-dried 20 mL vial equipped with a stir bar, in a nitrogen glovebag. To this vial dichloromethane (9.64 g, pre-dried with activated 3A molecular sieves and sparged with nitrogen) was added, and the mixture was stirred at ambient temperature at 300 rpm. Triethylammonium chloride (1.40 g) was slowly added to the stirring solution contained within the vial. The mixture was stirred at ambient temperature and pressure for 2.8 h, and then the conjunct polymer was extracted with 15 mL n-pentane (pre-dried with activated 3A molecular sieves). The conjunct polymer was extracted from the reaction mixture two more times; the total volume of n-pentane used was 45 mL. The combined n-pentane extracts were washed with 20 mL deionized water, followed by 10 mL of 0.1% $Na_2CO_3$, and then 10 mL of 0.1% $H_2SO_4$. The n-pentane layer was then dried over anhydrous $MgSO_4$, filtered through fiberglass, and concentrated under vacuum using a rotary evaporator. The amount of conjunct polymer extracted was 0.156 g, indicating 81% removal of the conjunct polymer from the ionic liquid. The chlorine concentration within the conjunct polymer was determined to be 14,200 ppm by the ion combustion method UOP991-12. The conjunct polymer was further analyzed by simulated distillation (ASTM D2887) and is shown in Table 1 below.

TABLE 1

Simulated distillation (ASTM D2887) of conjunct polymer samples

| Wt. % | $CP^{a,b}$ | $CP^{a,c}$ |
|---|---|---|
| $TBP^d$@0.5 | 163 | 167 |
| TBP@5 | 203.2 | 210.8 |
| TBP@10 | 219.8 | 231.4 |
| TBP@15 | 232 | 247.6 |
| TBP@20 | 241.2 | 261 |
| TBP@25 | 249.2 | 273.4 |
| TBP@30 | 258.2 | 284.2 |
| TBP@35 | 266.2 | 294.8 |
| TBP@40 | 275.2 | 304.6 |
| TBP@45 | 284.2 | 314.4 |
| TBP@50 | 292.4 | 324.8 |
| TBP@55 | 299.2 | 336 |
| TBP@60 | 303.8 | 347.4 |
| TBP@65 | 312.6 | 359.6 |
| TBP@70 | 323 | 373 |
| TBP@75 | 334.4 | 388 |
| TBP@80 | 347.8 | 405.2 |
| TBP@85 | 364.8 | 426 |
| TBP@90 | 388.2 | 453.2 |
| TBP@95 | 425.8 | 495.4 |
| TBP@99.5 | 531.4 | 585.8 |

$^a$CP = conjunct polymer,
$^b$CP isolated from ionic liquid generated in Example 2,
$^c$CP isolated from the n-pentane extraction described in Example 4 and
$^d$TBP = temperature boiling point at x wt. %

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for regenerating deactivated acidic ionic liquid catalyst containing conjunct polymer comprising:
    contacting the deactivated acidic ionic liquid catalyst containing the conjunct polymer with at least one Brønsted acid in a regeneration zone under regeneration conditions, the at least one Brønsted acid being derived from a mineral acid and containing at least one organic group, resulting in a mixture comprising regenerated acidic ionic liquid catalyst, the at least one Brønsted acid, and the released conjunct polymer; and
    separating the released conjunct polymer from the regenerated acidic ionic liquid catalyst and the at least one Brønsted acid.

2. The method of claim 1 further comprising removing the at least one Brønsted acid from the regenerated acidic ionic liquid catalyst.

3. The method of claim 2 wherein removing the at least one Brønsted acid from the regenerated acidic ionic liquid catalyst comprises thermally decomposing the at least one Brønsted acid.

4. The method of claim 2 further comprising recycling the regenerated acidic ionic liquid catalyst to a hydrocarbon conversion process.

5. The method of claim 2 further comprising recycling the at least one removed Brønsted acid to the regeneration zone.

6. The method of claim 1 wherein contacting the deactivated acidic ionic liquid catalyst containing the conjunct polymer with the at least one Brønsted acid comprises contacting the deactivated acidic ionic liquid catalyst containing the conjunct polymer with the at least one Brønsted acid and a hydrocarbon solvent immiscible in the ionic liquid.

7. The method of claim 6 wherein the hydrocarbon solvent comprises a paraffin having up to 10 carbon atoms, an aromatic, or combinations thereof.

8. The method of claim 6 further comprising separating the hydrocarbon solvent from the conjunct polymer.

9. The method of claim 8 further comprising recycling the separated hydrocarbon solvent to the regeneration zone.

10. The method of claim 8 wherein separating the hydrocarbon solvent from the conjunct polymer comprises distillation.

11. The method of claim 1 wherein the deactivated acidic ionic liquid catalyst containing the conjunct polymer is contacted with the at least one Brønsted acid in the presence of a catalyst.

12. The method of claim 1 wherein the regeneration conditions include at least one of a temperature in a range of from about −20° C. to 200° C., and a contact time of between about 10 minutes and about 24 hours.

13. The method of claim 1 wherein the mineral acid is HCl, HF, HBr, HI, $H_2SO_4$, $HNO_3$, $H_3PO_4$, fluorosulfonic acids, or combinations thereof.

14. The method of claim 1 wherein a conjugate base of the at least one Brønsted acid is selected from amines, phosphines, nitrogen containing heterocycles, phosphorous containing heterocycles, pyrrolidines, imidazoles, or combinations thereof.

15. The method of claim 1 wherein contacting the deactivated acidic ionic liquid catalyst containing the conjunct polymer with the at least one Brønsted acid takes place in the presence of a mineral acid from which the at least one Brønsted acid is derived.

16. The method of claim 1 wherein a molar ratio of the Brønsted acid to the deactivated acidic ionic liquid catalyst containing the conjunct polymer is greater than 1:1.

17. The method of claim 1 further comprising mixing the deactivated acidic ionic liquid catalyst containing the conjunct polymer with a miscible solvent before contacting the deactivated acidic ionic liquid catalyst containing the conjunct polymer with the at least one Brønsted acid.

18. A method for regenerating deactivated acidic ionic liquid catalyst containing conjunct polymer comprising:

contacting the deactivated acidic ionic liquid catalyst containing the conjunct polymer with at least one Brønsted acid and a hydrocarbon solvent in a regeneration zone under regeneration conditions, the at least one Brønsted acid being derived from a mineral acid and containing at least one organic group, resulting in a catalyst phase containing the acidic ionic liquid catalyst and the at least one Brønsted acid and an organic phase containing conjunct polymer and the hydrocarbon solvent;

separating the catalyst phase from the organic phase;

separating the hydrocarbon solvent from the conjunct polymer;

recycling the separated hydrocarbon solvent to the regeneration zone; and removing the at least one Brønsted acid from the catalyst phase to regenerate the acidic ionic liquid catalyst.

19. The method of claim 18 wherein contacting the deactivated acidic ionic liquid catalyst containing the conjunct polymer with the at least one Brønsted acid takes place in the presence of HCl.

20. The method of claim 17 further comprising at least one of recycling the regenerated acidic ionic liquid catalyst to a hydrocarbon conversion process, and recycling the at least one removed Brønsted acid to the regeneration zone.

* * * * *